United States Patent [19]
Connell

[11] Patent Number: 5,937,858
[45] Date of Patent: Aug. 17, 1999

[54] ORO/NASOPHARYNGEAL AIRWAY FOR ADMINISTERING/SAMPLING INHALENT/ EXPIRED GASES

[76] Inventor: Donald G. Connell, 937 Bridle Path Rd., Allentown, Pa. 18103

[21] Appl. No.: 08/985,829

[22] Filed: Dec. 5, 1997

[51] Int. Cl.⁶ .................................................. A61M 16/00
[52] U.S. Cl. ............................... 128/207.14; 128/200.26; 128/201.25; 128/207.18; 128/911
[58] Field of Search ......................... 128/207.14, 200.26, 128/201.18, 201.25, 201.26, 205.25, 206.2, 207.18, 205.12, 205.28, 206.11, 912; 600/532

[56] References Cited

U.S. PATENT DOCUMENTS

| | | | |
|---|---|---|---|
| 4,256,099 | 3/1981 | Dryden | 128/200.26 |
| 4,300,550 | 11/1981 | Gandi et al. | 128/207.18 |
| 4,821,715 | 4/1989 | Downing | 128/207.18 |
| 5,143,062 | 9/1992 | Peckham | 128/207.14 |
| 5,555,890 | 9/1996 | Schaller | 128/205.12 |
| 5,765,558 | 6/1998 | Psaros et al. | 128/207.14 |

*Primary Examiner*—John G. Weiss
*Assistant Examiner*—V. Srivastava
*Attorney, Agent, or Firm*—Warren W. Kurz

[57] ABSTRACT

An oro/nasopharyngeal airway comprises an arcuately shaped tubular member adapted for insertion into a patient's pharynx, either through the mouth or nasal passage, to prevent obstruction during the administration of anesthesia. According to a preferred embodiment, an inhalant gas, typically oxygen ($O_2$), is delivered to the airway via a gas line connected to the proximal end of the tubular member, while expired carbon dioxide ($CO_2$) is sampled in the patient's pharynx via a second gas line connected to the tubular member in the vicinity of its distal end. Preferably, the respective inhalant and expired gas lines are positioned within the interior of the tubular member and are integral parts thereof Alternatively, the airway defines two discrete and parallel lumens or conduits, one being adapted to be connected to an inhalant gas supply, and the other being adapted to be connected to a gas level-sensing device.

10 Claims, 3 Drawing Sheets ered to the patient's pharynx, and expired gases can be extracted from the pharynx for sampling purposes.

ORO/NASOPHARYNGEAL AIRWAY FOR ADMINISTERING/SAMPLING INHALENT/EXPIRED GASES

BACKGROUND OF THE INVENTION

1. Field of the Invention

The present invention relates to improvements in pharyngeal airways of the type used during surgical and other medical procedures to prevent obstruction of the pharynal region of the alimentary canal, for example, while a patient is under anesthesia. More particularly, the invention relates to a pharyngeal airway which, in addition to being adapted to maintain a patient's airway open during a medical procedure, is also adapted to administer an inhalant gas (e.g., oxygen) and/or sample an expired gas, i.e., carbon dioxide in the patient's pharynx so as to provide an early indication of an interruption of proper respiration or breathing.

2. Discussion of the Prior Art

During surgical procedures in which a patient is placed under general anesthesia, an anesthetist or anesthesiologist continuously administers a general anesthetic (e.g. sodium pentothal/muscle relaxant) and manages the patient's respiration or breathing. Often, an endotracheal tube is fitted into the patient's trachea for administering anesthesia and other drugs, and a mechanical ventilator is used to pump oxygen into the patient's lungs and to extract therefrom expired carbon dioxide. To ensure that proper ventilation is taking place, it is common for the anesthetist to monitor the respective levels of (i) oxygen saturation in the patient's blood and (ii) the expired carbon dioxide. Pulse oximetry is the technique most often used to detect the level of blood oxygenation, and capnography is commonly used to monitor the expired carbon dioxide level. Of the two types of monitors for detecting proper ventilation, the carbon dioxide monitor is far quicker to indicate an interruption of ventilation since oxygen saturation can remain at a normal or near normal level for several minutes after proper ventilation has ceased. On the other hand, an interruption in ventilation will almost immediately give rise to a precipitous drop in the carbon dioxide level.

An increasingly popular alternative to general anesthesia is Monitored Anesthesia Care (MAC) with sedation. It differs from general anesthesia in that (a) much shorter-acting anesthetics (e.g., propofol or midazalam) are used to place the patient in a deep state of anesthesia, and (b) the patient is not put on a ventilator, i.e., the patient breathes by himself, just as if sleeping. Though shorter acting, MAC drugs are nonetheless potent hypnotics and analgesics. With the ever-increasing number of out-patient surgeries, many types of surgical procedures that were formerly performed under general anesthesia are now performed using this newer technique. In administering these drugs, it will be appreciated that the anesthetist must be highly skilled in airway management and especially attentive to the patient's breathing since, as noted, the patient is required to breath on his own.

During MAC anesthesia procedures, oxygen is commonly delivered to the patient either through a facial mask or through a nasal cannula. Either of such delivery devices enables the patient to achieve maximum oxygenation. As in the case of general anesthesia, oxygen saturation is typically measured by pulse oximetry, using an infrared sensor which is usually attached to the patient's finger, ear or toe. When a mask is used for administering oxygen, the level of expired carbon dioxide can be easily monitored by placing a capnograph sample line inside the mask. When a nasal cannula is used for administering oxygen, one of the two nasal prongs can be connected to the capnograph sample line while the other prong supplies oxygen. While both of these devices (i.e. the facial mask and nasal cannula) can be highly effective in delivering oxygen and monitoring expired gas, both can be problematic under certain circumstances. For example, a facial mask can interfere with most surgical procedures involving the patient's face and, hence, is usually not used during such procedures. On the other hand, a split nasal cannula can only be used when both nasal passages are clear and the patient is not breathing through the mouth. When either nasal passage is closed or even partially obstructed, either oxygen delivery or carbon dioxide monitoring is compromised. Thus, it is apparent that a need exists for a device that is capable of delivering oxygen and/or monitoring the level of expired gas without presenting the problems identified.

During MAC with sedation procedures, a patient may become so sedate that breathing will become slow or even stop all together. When a respiration failure is detected (as may also occur during an obstruction or closure of the patient's airway, e.g. by the patient's tongue falling back in the pharynx), the anesthetist must be quick to respond. Usually, proper breathing can be restored by a simple jaw thrust or a repositioning of the patient's head. But sometimes a mechanical "airway" must be inserted into the patient's pharynx, either through the mouth or nose, to clear the obstruction and restore proper breathing. A typical mechanical airway comprises a soft rubber tube having a length sufficient to pass any obstruction in the pharynx and to allow normal respiratory gas exchange through the tube. Usually, such airways have an arcuate shape to conform to the shape of the alimentary canal. While being adapted to maintain an open, unobstructed air passage, conventional airways are not adapted to deliver oxygen or the like, or to monitor the level of exhalant gas. In fact, when a facial mask is used to administer oxygen and to sense the carbon dioxide level, the anesthetist must be quick to reapply such mask after removing it to insert a mechanical airway so as to assure continuous blood oxygenation and carbon dioxide monitoring.

SUMMARY OF THE INVENTION

In view of the foregoing discussion, an object of this invention is to provide an improved pharyngeal airway device which, in addition to being adapted to maintain an open airway passage, is also adapted to deliver oxygen or other inhalant gas directly to a patient's pharynx, and to monitor the level of exhalant (expired) gas in the vicinity of a patient's trachea where the carbon dioxide level is greatest.

Another object of this invention is to provide an improved mechanical airway which obviates the need for either facial masks or split nasal cannulas for delivering inhalant and monitoring the level of exhalant gases.

Another object of this invention is to provide an improved method for monitoring the level of expired gas from an anesthetized patient.

According to a preferred embodiment, the airway apparatus of the invention generally comprises a single channel, tubular member, preferably having an arcuate shape, which is adapted for insertion into a patient's pharynx, either through the mouth or nasal passage, to provide a mechanical airway which prevents obstruction during the administration of anesthesia. In contrast with conventional mechanical airways, the airway of the invention is provided with means for coupling a pair of gas lines to the interior channel of the airway through which oxygen or the like can be directly administered to the patient through the airway, and the level of exhalant gas ($CO_2$) can be sampled, again through the airway. Preferably, the inhalant gas line is connected to the proximal end of the airway, and the exhalant gas line is connected to the distal end of the airway. By virtue of its construction, the airway of the invention operates to maintain an open airway while simultaneously delivering optimum oxygenation, and providing for optimum detection of expired gas, so as to assure early detecting of a ventilation problem.

According to another embodiment of the invention, the tubular member which maintains an open airway has two side-by-side conduits or lumens which are spaced apart by a common septum or wall. Coupling means are provided for coupling an inhalant gas line to one conduit, and an exhalant gas sampling line to the other conduit.

In accordance with another aspect of the invention, an improved method for monitoring the level of expired gas during anesthesia is characterized by the step of sensing the expired gas level within the posterior pharynx region where the expired gas concentration is relatively high and the detection thereof is not significantly effected by the flow of inhalant gas.

The invention will be better understood from the ensuing detailed description of preferred embodiments, reference being made to the accompanying drawings in which like reference characters denote like parts.

DETAILED DESCRIPTION OF PREFERRED EMBODIMENTS

Figure 1A:
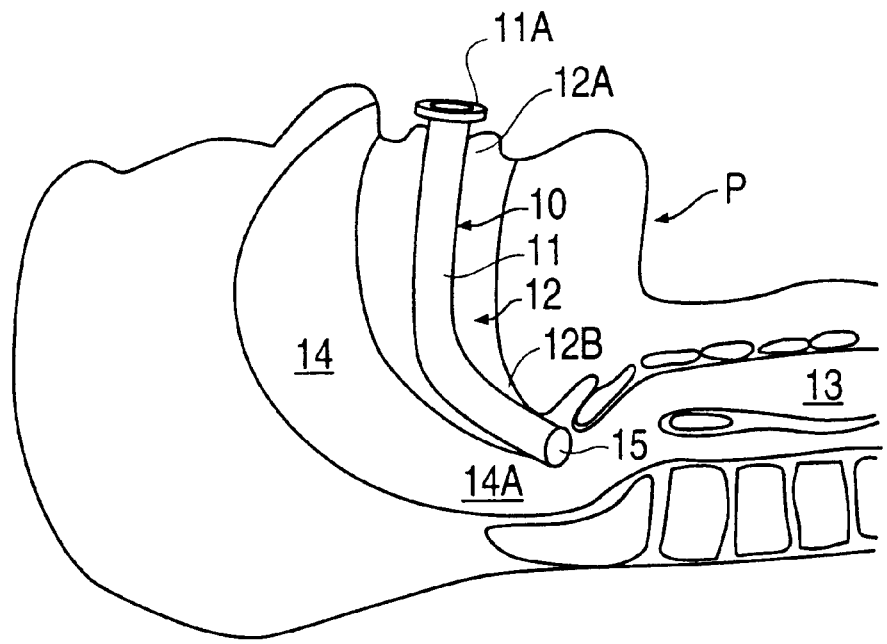
FIGS. 1A and 1B illustrate conventional oropharyngeal and nasopharyngeal airways positioned in the pharynx of a patient undergoing anesthesia.
Figure 1B:
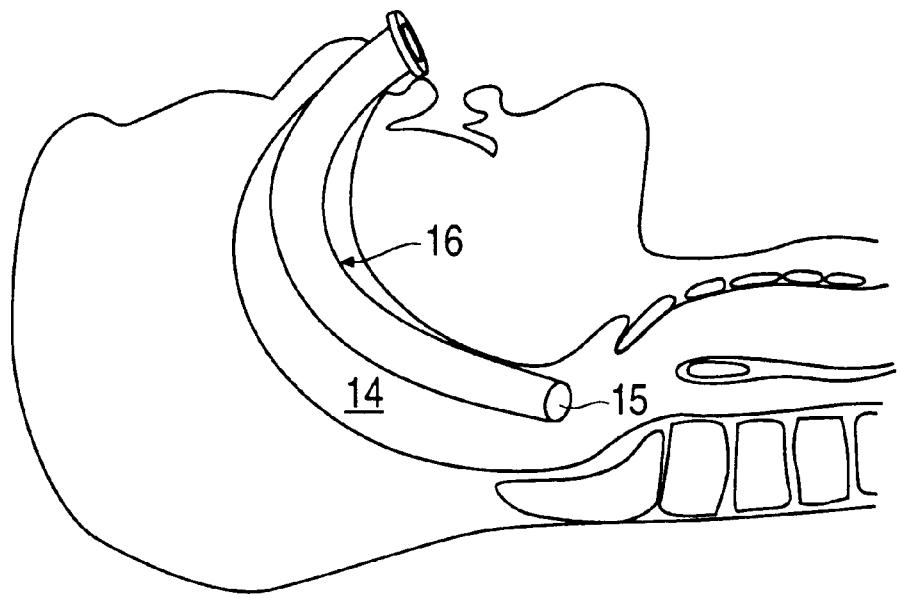

Referring now to the drawings and particularly to FIG. 1A, a conventional oropharyngeal airway 10 is shown positioned in the oral cavity 12 of a patient P. Airway 10 commonly comprises a relatively pliable tube made 11, for example, of latex, silicone rubber or a soft polyvinylidene fluoride (PVC) and having an outside diameter of about one inch, and an inside diameter of about ¾ inch. The length of tube 11 is typically about 6–8 inches so as to extend from the anterior pharynx region 12A, beginning at the entrance of the mouth, to the posterior pharynx region 12B, in the vicinity of the base of the tongue where the tongue joins with the posterior region of the nasopharyngeal cavity 14. Tube 11 is usually provided with a flared end 11A which abuts the patient's lips when the airway is fully inserted. The airway is often given an arcuate shape to conform somewhat to the pharyngeal passageway and in order to facilitate insertion. The wall of the airway is sufficiently rigid to prevent the patient's tongue from collapsing the tube wall and thereby obstructing the patient's alimentary canal (i.e., the patient's airway). In use, the airway also enables normal respiratory gas exchange through the conduit 15 defined by the tube structure. A conventional nasopharyngeal airway 16 is shown in use in FIG 1B. Airway 16 is virtually identical to airway 10, except that its diameter is somewhat smaller to facilitate insertion through the nasal passage.

Figure 2:
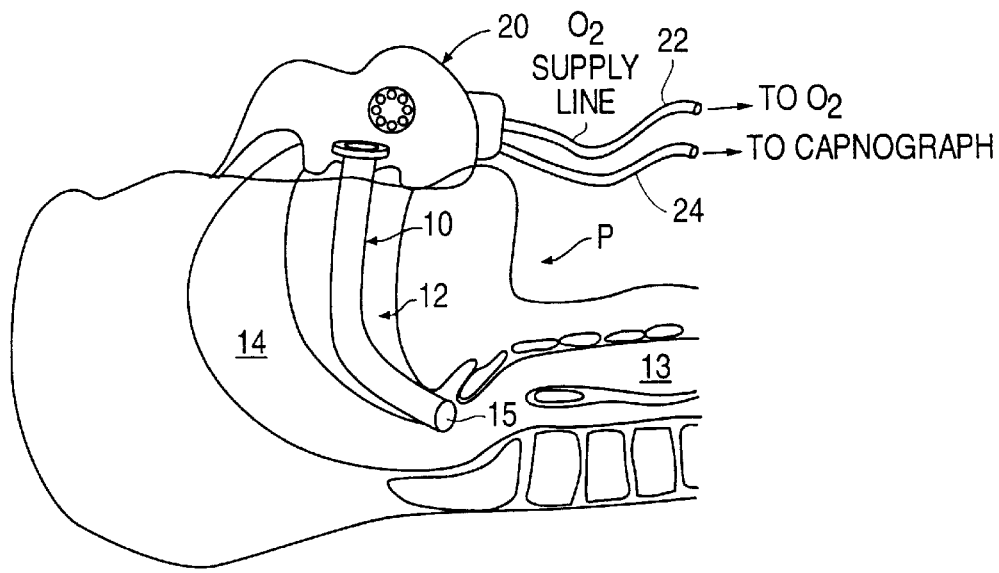
FIG. 2 illustrates the combined use of a conventional oropharyngeal airway and face mask for delivering an inhalant gas and for monitoring expired gas.

As noted above, a mechanical airway of the type described above is often used only after a patient has obstructed during the administration of anesthesia and/or other drugs and proper breathing has been interrupted. In FIG. 2, an oropharyngeal airway 10 is shown in use while a facial mask 20 has been applied to both (a) administer an inhalant gas, typically oxygen, which is provided to the mask through an inhalant gas line 22, and (b) monitor the level of carbon dioxide gas expired by the patient. An expired gas sampling line 24 is connected between the mask and a capnograph to detect the level of carbon dioxide within the mask. As may be appreciated, the need for both a sterile airway and mask increases the expense of the surgical procedure.

Figure 3:
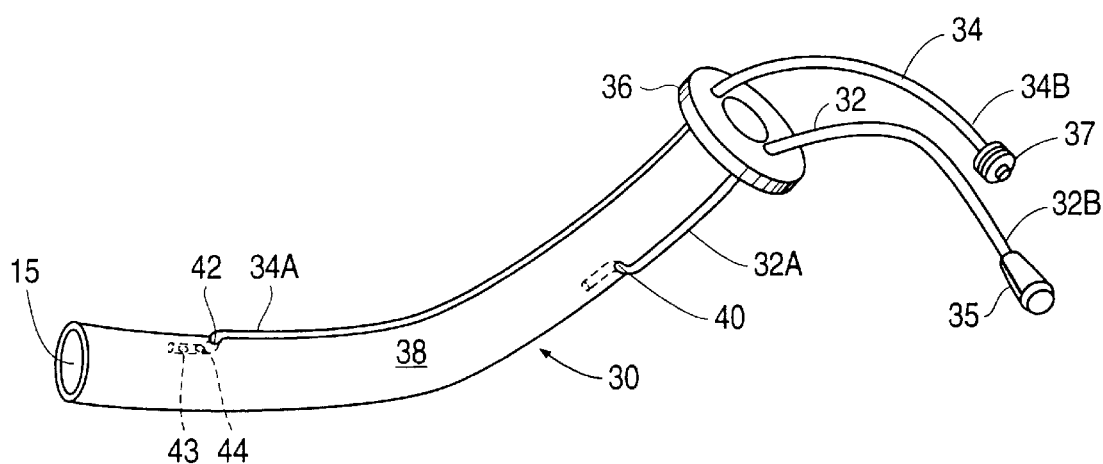
FIG. 3 is a perspective illustration of a pharyngeal airway structured in accordance with a preferred embodiment of the invention.

Now in accordance with the present invention, the need for the combination of (i) a mechanical airway to maintain an open air passage, and (ii) a facial mask (or a split nasal cannula) to both deliver oxygen or the like to a sedated patient, and to monitor the level of gas expired by such patient is totally obviated by the new and improved airway 30 illustrated in FIG. 3. As shown, airway 30 is similar in size, shape and construction to the conventional airways 10 and 16 described above. However, rather than operating to merely maintain an open air passage in the patient, the airway of the invention is adapted to deliver an inhalant gas, provided through an associated inhalant gas delivery line 32, as well as to sample the level of expired gas through an associated gas sampling line 34. Preferably, the inhalant gas sample line 32 is connected to the proximal end portion 30A of airway 32, and the expired gas sampling line 34 is connected to the distal portion 30B of the airway. By this arrangement, the inhalant gas does not swamp out the relatively low concentration of expired gas at the proximal end, and the expired gas is sampled at a location deep within the patient's pharynx, at the top of the trachea 13, where the expired gas concentration is significantly greater than at the anterior of the pharynx where the expired gas concentration is commonly monitored. Preferably, gas lines 32 and 34 pass through the flared portion 36 of the airway and run parallel to the tubular portion 38 of the airway, along the external surface thereof. One end 32A of the inhalant gas line enters a small hole 40 formed near the proximal end portion of the airway and terminates inside the tubular member in close proximity of the hole. The opposite end 32B of the inhalant gas line is fitted with a female coupling 35 which is adapted to be connected to another gas line which, in turn, is connected to an inhalant gas supply (not shown) which can supply inhalant gas, e.g., oxygen, at a rate of from 3–6 liters per minute. Similarly, one end 34A of the exhalant gas sampling line enters a small hole 42 formed in the distal portion of the airway and extends a short distance inside the tubular member. Preferably, the end portion 34A of the exhalant gas line is provided with two or three additional holes 43, 44, in the side wall thereof to assure exhalant gas can be sampled even if mucous or the like were to clog the end of the gas-sampling line. The opposite end 34B of the exhalant gas sampling line is fitted with a male coupling 37 which is adapted to be connected to a capnograph (not shown). Preferably, couplings 35 and 37 differ from each other to avoid any potential mistake in connecting the lines to the proper sources. Preferably, each of the gas lines 32,34 are made of polyethylene and have a diameter of about 2–5 mm.

Figure 4:
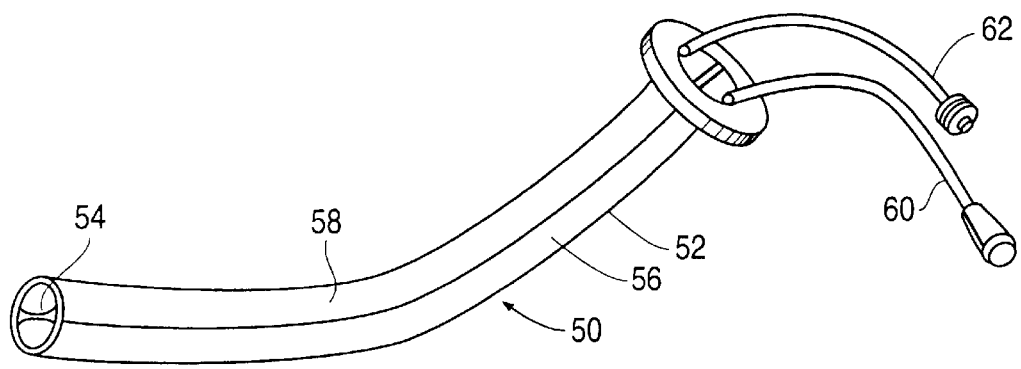
FIGS. 4 through 6 are perspective illustrations of alternative embodiments of the invention.
Figure 5:
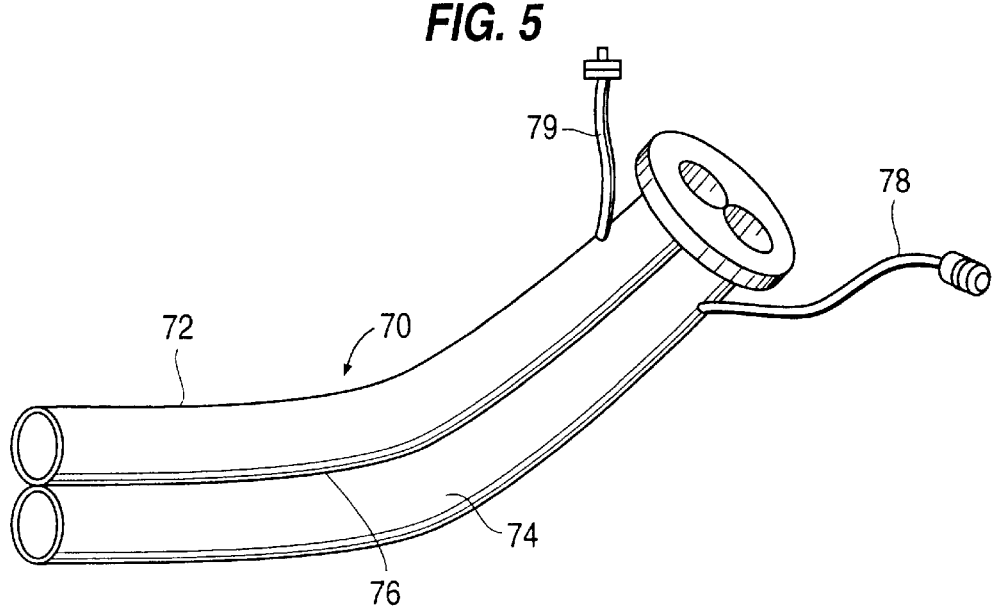
Figure 6:
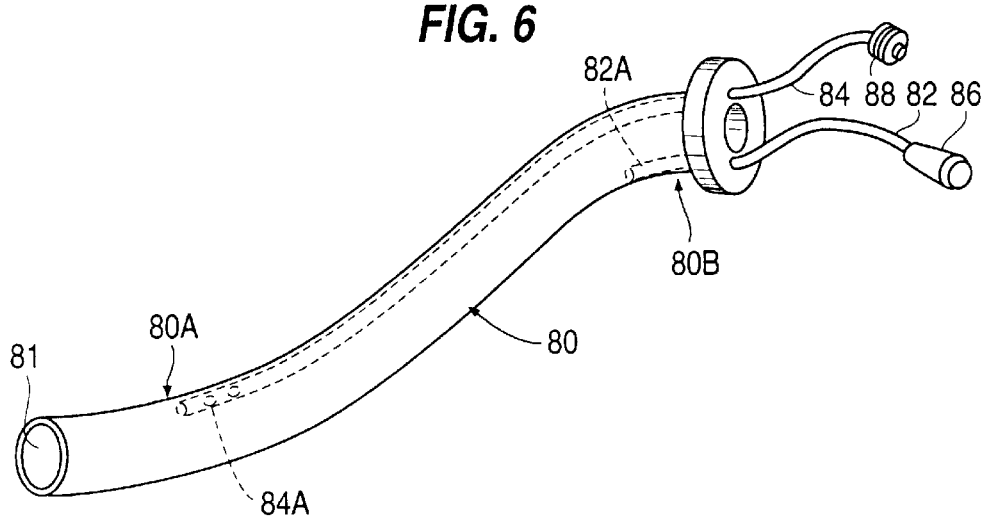

Alternative airways embodying the invention are shown in FIGS. 4 through 6. In FIG. 4, airway 50 is shown to comprise a tubular member 52 of circular cross-section. A septum 54 divides the internal conduit in half to define two side-by-side conduits 56, 58 which share a common wall, i.e., the septum. Inhalant and exhalant gas lines 60, 62 are connected to each of the conduits 56, 58 at the proximal end 50A of the airway. Because of the physical separation between the conduits, there is no need to guard against a washout of the exhalant gas signal by the incoming inhalant gas, and the exhalant gas sample line need not extend to the distal portion of the airway.

In FIG. 5, an airway 70 takes the form of two tubular lumens 72, 74 which are joined together along a common boundary or wall 76. Preferably, the dual lumen/conduit airways 50, 70 are produced by an injection molding process.

In FIG. 6, a highly preferred airway 80 defines a single internal lumen 81 containing a pair of gas lines 82, 84. Gas line 82 is adapted to be connected to an inhalant gas source through a female coupling 86. The opposite end 82A of gas line 82 is positioned within the proximal end of the airway's lumen and is held in place by a suitable adhesive, strap or other fastening means. Gas line 84 is adapted to be connected to a gas-sampling device through a male coupling 88. The opposite end 84A of gas line 84 is positioned within the distal end 80A of the airway, and is similarly affixed thereto by an adhesive, strap or other fastening means. It is also contemplated that those portions of gas lines 82, 84 located within the airway lumen can comprise tubes integrally formed in the inside wall of the airway, and the external portions of the two gas lines can be press fit into such tubes.

While the invention has been disclosed with reference to certain preferred embodiments, it will be appreciated that variations can be made without departing from the spirit of the invention, and such variations are intended to fall within the scope of the appended claims.

What is claimed is:

1. A pharyngeal airway apparatus comprising a tubular member adapted for insertion into a patient's pharynx, either through the oral or nasal passage, to prevent obstruction of the patient's airway during a medical procedure in which the patient is breathing naturally, and to enable the patient to breath naturally through the tubular member, said tubular member having a proximal open end and a distal open end and defining a continuous elongated breathing passageway between said ends, said distal end being adapted to be located within a patient's pharynx when the airway is in use while said proximal end remains outside the patient's oral or nasal passage, said tubular member having a pair of gas lines connected thereto, one gas line serving to administer an inhalant gas to said passageway while the other gas line serves to sample an expired gas within said passageway, said gas lines having respective distal ends that terminate within said passageway and are spaced apart such that the distal end of said one gas line is closer to the proximal end of said tubular member than the distal end of said other gas line.

2. The apparatus as defined by claim 1 wherein the distal end of said one of said gas lines terminates within said passageway in the vicinity of the proximal end of said tubular member, and wherein the distal end of said other of said gas lines terminates within said passageway in the vicinity of the distal end of said tubular member.

3. The apparatus as defined by claim 1 wherein said gas lines are connected to a flared portion of said tubular member at the proximal end thereof.

4. The apparatus as defined by claim 1 wherein each of the opposite ends of said gas lines is provided with a coupling adapted to connect to either an inhalant gas supply or to an exhalant gas sampling line through which expired gas can be presented to a measuring device.

5. The apparatus as defined by claim 1 wherein the respective inhalant and expired gas lines are positioned within the interior of the tubular member and are integral parts thereof.

6. The device as defined by claim 1 wherein said other gas line is provided with a plurality of axially spaced holes in a side wall thereof, said holes being located in the vicinity of the distal end of said other gas line.

7. A pharyngeal airway adapted for insertion into a patient's pharynx to prevent obstruction during anesthesia, said airway comprising (a) a tubular member defining an internal lumen through which a patient can breathe naturally during a medical procedure, said lumen extending from a proximal open end to a distal open end; (b) a first gas line having first and second opposing ends, said first end being adapted to be connected to an inhalant gas source; (c) a second gas line having first and second opposing ends, said first end of said second gas line being adapted to be connected to a gas-sampling device; and (d) means for supporting the respective second ends of said gas sampling lines within said lumen at locations axially spaced apart.

8. The apparatus as defined by claim 7 wherein said second end of said second gas line is located closer to said distal end than the second end of said first gas line.

9. The apparatus as defined by claim 7 wherein the respective first ends of said gas lines are connected to gas line couplings of different types.

10. A method for administering an inhalant gas to an anesthetized patient undergoing monitored anesthesia care (MAC) while simultaneously sampling the patient's expired gas, said method comprising the steps of (a) providing a pharyngeal airway comprising a tubular member through which a patient can breathe naturally during a medical procedure, said tubular member having a proximal open end and a distal open end and defining a breathing passageway between said ends; (b) positioning the distal open end of said airway in the posterior pharyngeal region of the patient; and (c) sampling the level of the patient's expired gas within said passageway in the vicinity of the distal end of said tubular member, while administering an inhalant gas to the passageway in the vicinity of the proximal end of said tubular member.

* * * * *